United States Patent [19]

Zimmerman

[11] Patent Number: 4,600,251
[45] Date of Patent: Jul. 15, 1986

[54] DENTAL TRAY RACK

[76] Inventor: James B. Zimmerman, 11 Lakeshore Plz., Kirkland, Wash. 98033

[21] Appl. No.: 507,775

[22] Filed: Jun. 27, 1983

[51] Int. Cl.⁴ .................................... A47B 81/00
[52] U.S. Cl. ................................. 312/209; 108/108; 211/88; 211/133; 211/208; 248/224.2; 312/128; 312/284; 403/231; 433/49
[58] Field of Search ............... 312/284, 209, 128, 283, 312/285; 182/92; 211/87, 88, 207, 208, 193, 13, 133, 107, 205; 108/107, 108, 110, 28, 144; 248/243, 224.2; 433/37, 49; 403/231

[56] References Cited

U.S. PATENT DOCUMENTS

| | | | |
|---|---|---|---|
| 41,027 | 12/1863 | Summers | 211/87 X |
| 317,906 | 5/1885 | Williams | 211/87 X |
| 320,141 | 6/1885 | Keck | 312/284 |
| 412,461 | 10/1889 | Canon | 312/284 X |
| 733,037 | 7/1903 | Heimann | 248/243 |
| 1,066,806 | 7/1913 | Freud | 211/193 X |
| 1,547,103 | 7/1925 | Dindinger | 211/133 X |
| 1,657,939 | 1/1928 | Rockwell | 248/243 X |
| 1,776,491 | 9/1930 | Doge | |
| 2,061,957 | 11/1936 | Brown | 312/284 X |
| 2,398,091 | 4/1946 | Gluckman | 211/88 X |
| 2,470,679 | 5/1949 | Beers | 433/37 |
| 3,057,671 | 10/1962 | Forman | 312/284 X |
| 3,153,177 | 10/1964 | McFadyen | |
| 3,629,943 | 12/1971 | Gindea | |
| 3,704,519 | 12/1972 | Lystager | |
| 3,895,774 | 7/1975 | Sharp | 108/108 X |
| 4,051,789 | 10/1977 | Howitt | 248/243 X |
| 4,150,752 | 4/1979 | Breining et al. | |
| 4,154,356 | 5/1979 | Schieve | 211/88 X |
| 4,156,515 | 5/1979 | Mochly | 108/108 X |
| 4,193,198 | 3/1980 | Bauer | 211/13 X |
| 4,377,241 | 3/1983 | Schreiner | 211/133 |

FOREIGN PATENT DOCUMENTS

| | | | |
|---|---|---|---|
| 451008 | 9/1948 | Canada | 211/133 |
| 1263403 | 3/1968 | Fed. Rep. of Germany | 403/231 |
| 928973 | 12/1947 | France | 433/37 |
| 1095285 | 5/1955 | France | 211/13 |
| 1385605 | 12/1964 | France | 211/13 |
| 321355 | 6/1957 | Switzerland | 108/144 |
| 286235 | 3/1928 | United Kingdom | 211/13 |
| 380407 | 9/1932 | United Kingdom | 433/49 |

Primary Examiner—William E. Lyddane
Assistant Examiner—Thomas A. Rendos
Attorney, Agent, or Firm—Dowrey and Cross

[57] ABSTRACT

A rack for holding dental impression trays includes a rectangular block having apertures therein to receive the handles or tubes extending from the trays and to cantilever the trays from the rack. A paired arrangement of apertures can accommodate a tray having both a handle and tubes. A base supporting the rack upright has wells therein for holding water which, together with a dome enclosing the rack, provide a moist atmosphere for the impression material, where needed. The rack can be free-standing or wall-mounted. One embodiment of the rack adapted for wall-mounting can be inexpensively manufactured of plastic by extrusion.

10 Claims, 4 Drawing Figures

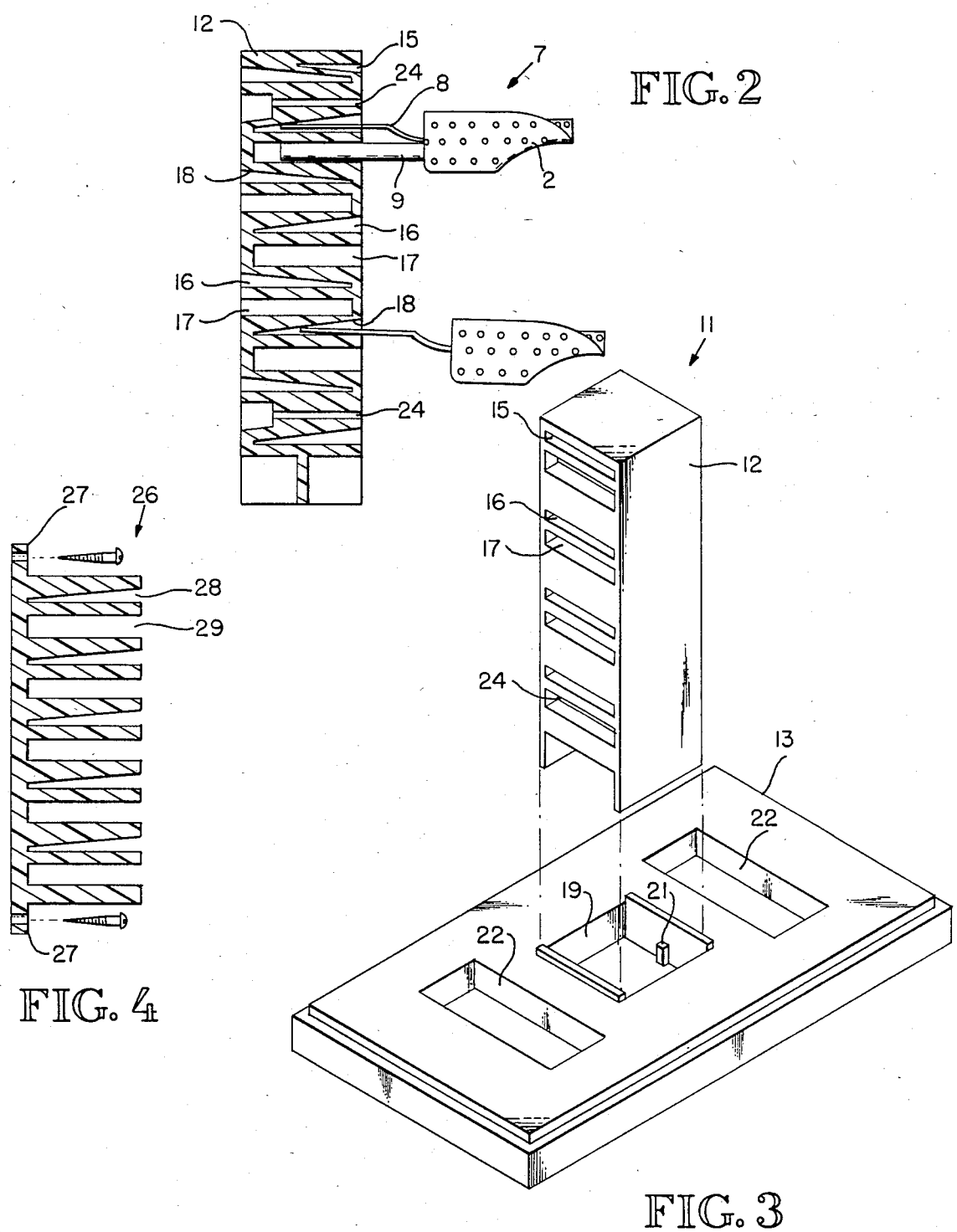

DENTAL TRAY RACK

FIELD OF THE INVENTION

This invention relates to the field of supporting racks and implement holders, and more specifically to the field of racks for holding dental implements.

DESCRIPTION OF THE PRIOR ART

In making a denture or other prosthesis, a dentist typically takes an impression of the patient's jaw with material held in a tray specifically designed for this purpose. Some dental impression trays have a pair of tubes extending therefrom, through which water is circulated to aid in setting the impression material. Other trays have a single flat handle extending therefrom. A third variety of dental impression trays have both a flat handle and a pair of tubes extending beneath the handle.

After the tray is removed from a patient's mouth, it must be held in such a way as to allow air to circulate around it for the material therein to set properly. The typical system for holding a tray is the extending of the tray from a countertop with a heavy weight resting on the counter upon its handles or tubes. Obviously, it is easy for one passing by to knock the tray to the floor or otherwise disrupt the impression setting process. A further disadvantage of this tray supporting scheme is that it cannot be utilized by a person having only one free hand.

A further difficulty in holding dental impression trays while the material therein sets is the provision of a moist atmosphere, which is advantageous for the setting of certain commonly used impression materials. The above described countertop scheme does not include any means for providing ambient moisture. U.S. Pat. No. 1,776,491 to Doge discloses a receptacle for holding a tray in a moist atmosphere, but trays cannot easily be inserted in this cumbersome receptacle, and certainly cannot be inserted with a user's free hand if his other hand is busy, as is often the case for personnel in a dental office or lab. Likewise, trays are not easily removed from the device.

BRIEF DESCRIPTION OF THE INVENTION

The present invention provides a unique, effective and inexpensive alternative to the makeshift manner of holding trays on a countertop commonly used in the dental profession, and to the cumbersome receptacle of the Doge patent. In one embodiment, the invention includes a rectangular block having apertures therein to receive the handles or tubes extending from dental trays and cantilever the trays from the rack. A base supporting the rack upright has wells therein for holding water which, together with a dome enclosing the rack, provide a moist atmosphere for the impression material, where needed.

In a preferred embodiment, the rack of the present invention can be free-standing or wall-mounted. A second embodiment of the invention is especially adapted for wall-mounting, and can be inexpensively manufactured by extrusion methods well known in the plastics manufacturing art.

The dental tray rack of the present invention is well suited for all of the above described tray handle configurations, and the apertures therein are of a special design, having a slanted surface for sure retention of the trays. The rack does not require that a user have both hands free, making it convenient for dental personnel in the process of taking impressions.

BRIEF DESCRIPTION OF THE DRAWINGS

FIG. 2 is a side cross-sectional view of the rack of FIG. 1, with the base and dome removed.

FIG. 3 is an exploded view of the rack of FIG. 1.

FIG. 4 is a side cross-sectional view of a second preferred embodiment of the invention.

DESCRIPTION OF THE ILLUSTRATED EMBODIMENTS

Figure 1:
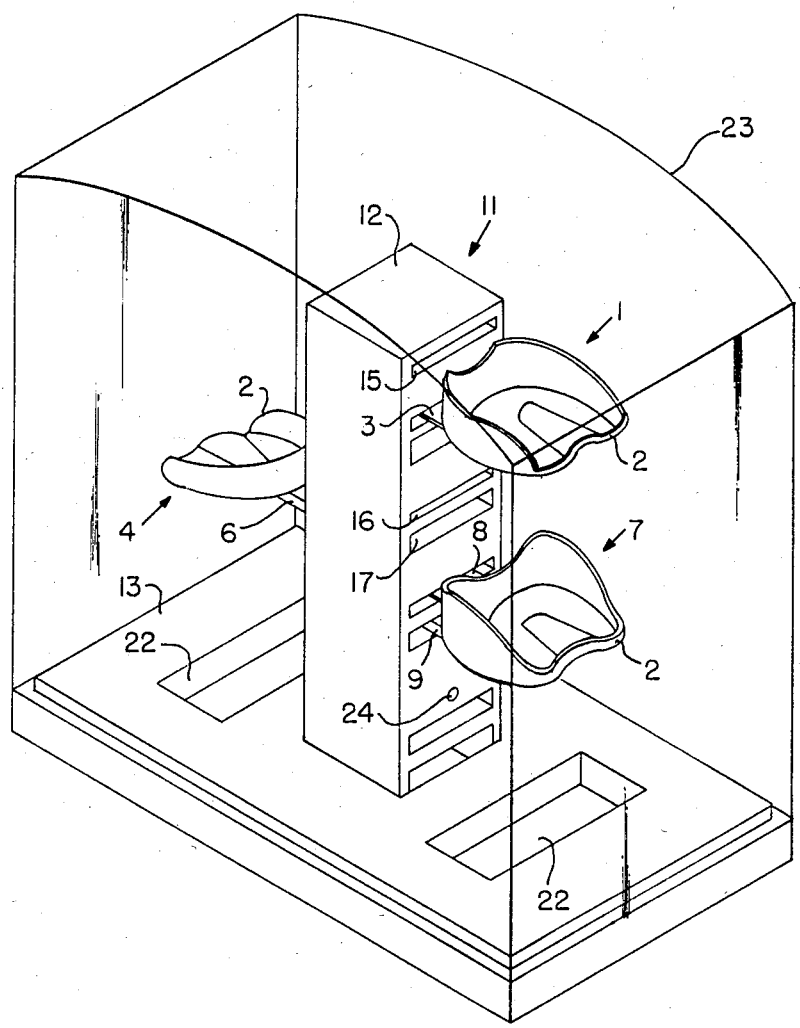
FIG. 1 is a perspective view of a first preferred embodiment of the invention.

Although the rack of the present invention may be found useful for holding articles other than those used in the dental profession, the following description of the illustrated embodiments will be directed toward this particular use of the invention for illustrative purposes.

Referring to FIGS. 1-3, a first type of dental tray 1 includes a receptacle 2 for holding molding material, and a flat handle 3 protruding from the receptacle 2 in a direction parallel to the general plane of the receptacle 2. A second type of tray 4 includes a similar receptacle 2, and a pair of tubular protrusions 6, while a third type of tray 7 includes both a handle 8 and a pair of tubes 9 below and parallel to the handle 8. A rack 11 according to a first preferred embodiment of the invention includes an upright member 12 supported in a base 13, both of which are preferably constructed of a plastic material by any commonly known method, such as injection molding. Preferably, the upright member 12 is a rectangular block having alternately on two opposing vertical sides a series of horizontal apertures of triangular and rectangular cross-sections 16 and 17. The triangular apertures 16 are narrow in a vertical direction, and have upper surfaces 18 which slope downward and back into the upright member 12 to securely hold a dental tray handle 3 or 8 with the receptacle 2 in proximity to the face of the upright member 13, as is best seen in FIG. 2. A right triangular cross-sectional shape combines the convenience of a wide opening for easy insertion of the handle 3 or 8, with the security of a narrow slot for cantilevering the substantially flat tray handle.

In the illustrated embodiment, the dimensions of the triangular and rectangular apertures 16 and 17 are chosen to accommodate dental impression tray handles 3, 8 and tubes 9 respectively. For the triangular apertures, it has been found satisfactory to have the legs of the triangle measure approximately 1½ inches and 5/16 inch. A 1½ inch by ¼ inch rectangular cross-section for the rectangular apertures 17 has been found to be adequate for accepting tray tubes 9.

In a preferred embodiment, four or more pairs of triangular apertures 16 and rectangular apertures 17 immediately above will be arranged equidistantly and nested alternately on each side of the upright member 12, extending upward approximately 5 to 5½ inches from the base 13. The paired aperture arrangement offers the unique advantage of allowing the rack 11 to hold not only trays having either a handle or tubes extending therefrom, but also those that have both. For full utilization of available space, a foreshortened triangular aperture 15 can be included at the top of the rack 11.

The base 13 is preferably rectangular, having in its center a cavity 19 for receiving the upright member 13. A key 21 molded into the sidewall of the cavity 19 mates with a corresponding groove (not shown) on one side of the upright member 13, to ensure its proper positioning therein. If desired, hollow portions (not shown) on the underside of the base 13 can be filled by the user with casting materials commonly found in dental offices to weight the base for stability. Although this is advantageous in that it is economical, the base, of course, can be weighted by any well known means by the manufacturer or the user.

A well 22 on either side of the cavity 19 holds water and, together with a preferably transparent dome 23 enclosing the rack 11, will provide a humid atmosphere for impression setting, if desired.

While the base 13 and upright member 12 can be integrally formed, a removable base 13 is advantageous in that the upright member 12 can then be free-standing or wall-mounted by screws, nails or the like, inserted in screw holes 24 located near the top and bottom portions of the upright member 12, at the user's option.

A second embodiment of the invention specially adapted for wall mounting is illustrated in FIG. 4. A plastic rack 26 which is extruded in a cross-sectional shape forming alternating triangular and rectangular slots 28 and 29 of the shape described for the apertures 6 and 7 of the first embodiment has mounting tabs 17 on its upper and lower edge for the insertion of a screw, nail or the like. The rack 16 can be made with any desired number of slots.

Although the invention has been described with respect to specific embodiments put to a particular use, modifications to these embodiments can, of course, be made within the scope of the invention.

What is claimed is:

1. A curing rack for supporting a dental impression tray, said tray generally including receptacle means for holding a mass of dental impression molding material therein for forming and setting and means forming at least a first elongated lateral protrusion extending therefrom a substantial distance in a direction generally parallel to the general plane of said receptacle, said rack comprising
    a support member having an elongated body of substantial thickness with at least one generally planar external surface,
    means for mounting said support member in a rigid upright position with said one external surface extending in a generally vertical direction, and
    means defining at least one aperture in the body of said support member extending generally horizontally into said one external surface, said aperture having a generally rectangular cross section in a plane parallel and a generally triangular cross section in a plane perpendicular to said one external surface, the cross section at said one external surface being at least large enough to permit unobstructed insertion and withdrawal of said first protrusion, said aperture having an upper surface which slopes downward and backward from one end at said one external surface to a second end interiorly of said support member for engaging an upper free end portion of said first protrusion between the first and second ends of said sloping surface, said sloping upper surface, aperture cross-sections and aperture depth cooperating with said first protrusion for supporting said receptacle means in a cantilevered fashion adjacent and spaced from said one external surface with the general plane of said receptacle means disposed generally horizontally, whereby
    a dental impression tray containing unset impression material may be rapidly mounted in said support member by unobstructed linear insertion of the first protrusion into said aperture and engagement between the first protrusion and the aperture surfaces.

2. A rack according to claim 1 wherein said mounting means includes a generally flat base member engagable with said support member to hold said support member in a generally upright position perpendicular thereto, said base member including means for holding water in proximity to said external surface of the support member, said rack further comprising means forming an enclosure over said support member and said water holding means for providing a humid atmosphere to facilitate setting of the dental impression molding material.

3. The rack according to claim 1 or 2 wherein the body of said support member includes;
    at least two of said generally external surfaces in opposite facing parallel spaced relation;
    each said external surface being provided with at least one said aperture with said apertures being in vertically spaced relation, whereby
    said support member is adapted to support at least two of said receptacle means cantilevered in opposite directions respectively from said planar surfaces.

4. The rack according to claim 3 wherein each said external surfaces is provided with a plurality of said apertures extending alternately in vertically spaced relation into said external surfaces.

5. A rack according to claim 1 wherein said mounting means includes means for mounting said support member against a vertical wall.

6. A rack according to claim 1 wherein said means forming at least said first lateral protrusion includes an upper lateral protrusion and at least one lower lateral protrusion parallel to and adjacent said upper protrusion, and wherein said at least one aperture comprises a first aperture and said means defining said at least one aperture further includes means defining a second generally horizontal aperture below said first aperture in the body of said support member extending generally horizontally into said one external surface, said first and second apertures comprising a set of vertically spaced apart apertures positioned to receive said upper and lower protrusions respectively.

7. The rack according to claim 6 wherein the body of said support member includes;
    at least two of said generally planar external surfaces in opposite facing parallel spaced relation,
    each said external surface being provided with at least one said set of apertures with said sets being in vertically spaced relation, whereby
    said support member is adapted to support at least two of said receptacle means cantilevered in opposite directions respectively from said planar external surfaces.

8. The rack according to claim 7 wherein each said external surface is provided with a plurality of said sets of apertures, each said set extending alternately in vertically spaced relation into said planar external surfaces.

9. The rack according to claim 8 wherein said mounting means includes a generally flat base member engagable with said support member to hold said support member in a generally upright position perpendicular thereto, said base member including means for holding water in proximity to said planar external surfaces of the support member, said rack further comprising means forming an enclosure over said support member and said water holding means for providing a humid atmosphere to facilitate setting of the dental impression molding material.

10. A curing rack according to claim 6 wherein said second aperture has a generally rectangular cross-section in a plane perpendicular to said one external surface.

* * * * *